United States Patent [19]

Hollander

[11] Patent Number: 5,334,347

[45] Date of Patent: Aug. 2, 1994

[54] ELECTRIC DISCHARGE DEVICE

[76] Inventor: Brad C. Hollander, 13213 Constable Ave., Granada Hills, Calif. 91344

[21] Appl. No.: 907,672

[22] Filed: Jul. 2, 1992

[51] Int. Cl.$^5$ .............................. A61L 2/10; A61L 9/20
[52] U.S. Cl. .......................................... 422/24; 422/5;
422/121; 55/279; 250/455.11
[58] Field of Search .................. 422/4, 22, 24, 186.04,
422/186.3, 120, 121, 168, 5; 55/101, 102, 128,
129, 140, 279, 385.7, DIG. 1; 250/432 R,
455.11, 504 R, 428

[56]  References Cited

U.S. PATENT DOCUMENTS

| | | | |
|---|---|---|---|
| 3,576,593 | 4/1971 | Cicirello | 422/24 X |
| 3,983,385 | 9/1976 | Troue | 250/428 X |
| 4,118,191 | 10/1978 | Böhnensieker | 55/102 X |
| 4,121,107 | 10/1978 | Bachmann | 250/504 X |
| 4,179,616 | 12/1979 | Coviello et al. | 422/186.3 |
| 4,227,446 | 10/1980 | Sone et al. | 422/121 X |
| 4,591,721 | 5/1986 | Wong | 250/373 |
| 4,990,313 | 2/1991 | Pacosz | 422/121 |
| 5,144,146 | 10/1992 | Wekhof | 422/24 X |

OTHER PUBLICATIONS

A. R. Dennington, "High Relative Humidity In Walk-in Refrigerators", Refrigerating Engineering, Jan., 1941, No. 41.

Arthur W. Ewell, Ph.D., "Researches on Ultra Violet Light And Ozone", Refrigerating Engineering, May, 1941.

Articles re quantifying health effects, airborne microorganisms and indoor air quality.

Information on disinfection, insect traps, circuitry for UV radiators and hazards from ultraviolet radiation prior art.

Primary Examiner—Robert J. Warden
Assistant Examiner—E. Leigh Dawson
Attorney, Agent, or Firm—Spensley Horn Jubas & Lubitz

[57] ABSTRACT

Aspects of the present invention are found in an electric discharge device comprising an envelope containing an electrode, a vaporizable material, and means for regulating the internal thermal condition so as to increase radiation output while improving the lifetime of the device. Further according to the invention, an electric discharge device is adapted to provide air sterilization in a vehicle's air conditioning system.

29 Claims, 6 Drawing Sheets

ELECTRIC DISCHARGE DEVICE

BACKGROUND OF THE INVENTION

1. Field of the Invention

This invention relates generally to electric discharge devices and more particularly the invention relates to such devices used in air sterilization.

2. Description of the Related Art

One type of electric discharge device utilizing mercury vapor is provided thermionic electrodes and has a starting gas therein such as argon, krypton, xenon, or neon. Such devices are efficient sources of visible light and emit in addition ultraviolet light which is useful in therapy, photo-chemistry, sterilization, irradiation of foodstuffs or the like. When desired, a luminescent material, such as a fluorescent or a phosphorescent material, is associated with the device to transform the ultraviolet light into visible light which complements and supplements the visible light emitted by the discharge in the device.

Typically, an electric discharge device has two primary parts, the tube and the base. The tube is commonly embodied as fluorescent light bulbs and tubes. Other common embodiments are ultraviolet tubes used in tanning booths, and grow-lamps for plants. These tubes are made in standard sizes and power capabilities, and have standardized outputs. Tubes having both elongated forms and bulb form are well-known in the art.

The base is designed so that the tube may be easily installed and removed, while holding the tube firmly during other times. The base typically incorporates a ballast. The ballast is an electrical component that converts a standard power input (i.e. 117 V, 0.10 A AC household current) to a form appropriate to the tube.

In certain types of electric discharge devices the energy input and the heat dissipating characteristics are in such relation that the envelope is at an elevated temperature and the gaseous vapor therein is at an elevated pressure, such as atmospheric pressure, during the operation of the device.

Container glasses which are highly heat resistant, chemically inert with respect to the hot, ionized metal vapor and which transmit ultraviolet light are desirable for use in such devices. Glasses which have a high transmission characteristic for ultraviolet rays typically age rapidly when subjected to such rays of shorter wave length. Further, these ultraviolet transmitting glasses typically have too low a softening temperature and are not inert to the hot mercury vapor and to other hot metal vapors which may be present in the lamp, such as cesium, cadmium, or zinc vapor. On the other hand, glasses which are inert to such metal vapors and which have a high softening temperature typically do not transmit enough ultraviolet at the thicknesses required in lamp containers to make the lamp useful as an ultraviolet generator.

Ultraviolet tubes are generally filled with mercury vapor. When an electrical potential difference is created across the tube, the mercury atoms are excited and emit ultraviolet radiation. The amount of radiation emitted is generally proportional to the power applied. Therefore, it is expected that a more powerful ultraviolet tube results, given a constant voltage, by simply increasing the current of the device.

However, as the power is increased, so too increases the heat produced. If too much heat is produced, the tube may enter a thermal runaway condition, resulting in decreased tube life. Therefore, the heat produced as a side effect practically limits the current of such tubes to 400 mA. This limit on the current also then limits the radiation output.

Another problem in electric discharge devices is skin-effect cooling. In skin-effect cooling, air moving across the outside of a tube causes the ultraviolet output level to drop. It is known that if the ambient temperature drops below 72° F. or air is blown over the tube, ultraviolet output drops at an extremely rapid rate —as much as a 75% depreciation of output at approximately 58° F.

An additional problem of electric discharge devices has been ozone creation. The energy below 230 nm radiated by these tubes apparently leads to the creation of ozone outside the tube.

Although it has long been known that electric discharge devices may be used for air sterilization, their actual implementation has been fairly limited. One reason for this has been some of the technological difficulties already discussed. Skin-effect cooling is one stumbling block in using electric discharge devices in many applications such as air sterilizers. Because of skin-effect cooling, 2 to 4 times as many tubes must be used for equal output, and the tubes must be replaced every 2500 hours. The high cost of extra tubes and the maintenance costs have limited the practicality of ultraviolet air sterilizers. One common usage of electric discharge devices as air sterilizers is in operating rooms and hospitals. However, higher output tubes used in these applications produce large amounts of ozone.

Table 1 shows the dosage of 254 nm ultraviolet radiation necessary to kill several common air contaminants. As can be seen, a dose of at least 11 $\mu W/cm^2$ is necessary to sterilize air containing these contaminants. However, the kinds of devices used for this purpose are very limited. Such devices cannot be used in such general purpose applications as air sterilization in smaller systems such as in automobiles and in trucks. Nonetheless, these other areas suffer from the same kinds of problems as hospital operating rooms. That is, they suffer from germs, mildew and odors.

This problem has become especially acute in vehicles. Vehicle air conditioning systems have become very efficient. However, this efficiency has led to very damp evaporator coils and drip pans of these air conditioner systems. Such damp areas become breeding grounds for mold and fungi, which emit foul odors and can even lead to disease. Typically, vehicle air conditioners are treated with chemicals to reduce or eliminate the mold and fungi. However, these chemicals have only temporary effect—typically less than one year, and must be reapplied. Furthermore, use of such chemicals may have harmful environmental and human-health side-effects. Use of the chemicals is inconvenient since application must be made directly to the evaporator coil and drip pan—parts which are typically not readily accessible.

Electric discharge devices have not been considered for removal or elimination of mold and fungi that cause odors growing in or around the evaporator coil of vehicle air conditioners. One reason is that the electrical system of a vehicle has not been well suited as a supply to electric discharge devices. A second reason is the harsh operating environment. Vehicle air conditioning systems typically operate at 20°–30° F. Electric discharge device output usually drops to near 0 at 20° F. The interior of the vehicle may be well over 140° F.

This broad operating range has generally been unsuitable for electric discharge devices. A third reason is that the compact design of vehicle air conditioning systems typically do not allow for the addition of bulky electric discharge devices. A fourth reason is that the physical instability of vehicles—bumps, jars, shakes—are generally considered poor sites for electrical discharge devices. A fifth reason is that the electric discharge device typically create large E-fields and emit large amounts of RF. The E-fields and the RF interrupt the operation of other electronic devices.

TABLE 1

| Bacteria | Dose ($\mu W/cm^2$) | Bacteria | Dose ($\mu W/cm^2$) |
| --- | --- | --- | --- |
| Bacillus anthracis | 45 | Pseudomoneas fluorescens | 35 |
| B. megatherium (veg.) | 11 | Salmonella enteritis | 40 |
| B. megatherium (spores) | 27 | S. typhosa-Typhoid fever | 22 |
| B. parathyphosus | 32 | S. paratyphi-Enteric fever | 32 |
| B. subtilis (spores) | 70 120 | S. typhimurium | 80 |
| Clostridium tetani | 130 | Sarcina lutee | 197 |
| Corynebact. diptheriae | 34 | Serratia marcescens | 24 |
| Eberthella typhosa | 21 | | |
| Escherichia coli | 30 | Shigella dysenteriae Dysentery form | 22 |
| Leptospira Spp.-Infectious jaundice | 32 | | |
| Micrococcus candidus | 61 | Shigella flexneri Dysentery form | 17 |
| Micrococcus piltonencis | 81 | Shigella paradysenteriae | 17 |
| Micrococcus sphaeroides | 100 | Spirillum rubrum | 44 |
| Mycobacterium tuberculosis | 62 | Staphylococcus albus | 18 |
| Neisseria catarrphalis | 44 | Staphylococcus aureus | 26 |
| Phytomonas tumefaciens | 44 | Streptococcus hemolyticus | 22 |
| Proteus vulgaris | 26 | Streptococcus lactis | 62 |
| Pseudomonas aeruginosa | 55 | Streptococcus viridans | 20 |
| Yeasts | | | |
| Common yeast cake | 60 | Mycobacterium tuberculi | 100 |
| Saccharomyces ellipsoideus (Bakers yeast) | 60 | Vibrio comm-Cholera | 34 |
| Saccharomyces cerevisiae (Bakers yeast) | 60 | Various algae Diatoms Green algae | 3600–6000 |
| Torula sphaeric (as found in milk and cream) | 23 | Blue algae Worms Nematode eggs | 400 |
| Protozoa | | | |
| Paramecium | 640–6000 | | |

SUMMARY OF THE PREFERRED EMBODIMENT

The object of the present invention is to provide an electric discharge device capable of emitting a large quantity of ultraviolet rays, while also providing a long, useful operating life over a wide temperature range.

Yet another object of the present invention is to provide for an air sterilizer of compact design that may be used for wide applications such as in motor vehicles.

These and other objects and advantages are achieved in an electric discharge device which, in accordance with a preferred embodiment of the present invention, incorporates a cooling region and is tolerant of high temperature and current. The cooling region causes ultraviolet output to increase while improving tube longevity so that problems with high temperature degradation and low ultraviolet output are solved. A gaseous convection current is produced in the tube when current is applied. Gas between the terminals is excited and emits radiation and heat.

Still further objects and advantages attaching to the device and to its use and operation will be apparent to those skilled in the art from the following particular description.

DESCRIPTION OF THE PREFERRED EMBODIMENT

The preferred electric discharge device comprises an elongated tubular container consisting of a quartz envelope. The preferred tube has two thermionic electrodes sealed therein at the ends thereof and a starting gas therein, such as argon, neon or krypton, or a mixture of such gases. The tube also has a quantity of vaporizable metal therein, preferably mercury, the vapor of which emits visible and ultraviolet light during the operation of the device. Preferably the quantity of metal is such that it is wholly vaporized at the operating temperature of the tube.

The electric discharge device further comprises a ballast. The ballast contains electrical circuitry which converts a standard power input to a character suitable for use with the tube. In the preferred embodiment, further change is made to the power input. Electricity is delivered at a standard of 60 Hz. The preferred ballast changes this frequency to 50–300 kHz. This high frequency allows the mercury in the tube to fire and stay on at all times without requiring high start-up temperatures.

It has been found that such a ballast, if used with standard tubes, increases the efficiency of the tube. Output of standard tubes can increase as much as 10–20% when used with a high frequency ballast.

When the improved ballast is combined with the improved tube, not only does output increase but tube life is extended greatly. Output increases 10–200% over standard electric discharge devices, and tube life is as much as 30,000 hours.

An additional benefit of the high frequency ballast is reduced ozone emissions. It is not entirely understood why, but it appears that an electrical frequency of over 25 kHz reduces ozone creation. In fact, it has been found that almost no ozone (0.01 ppm) is created when a device embodying the invention is operated.

Figure 1:
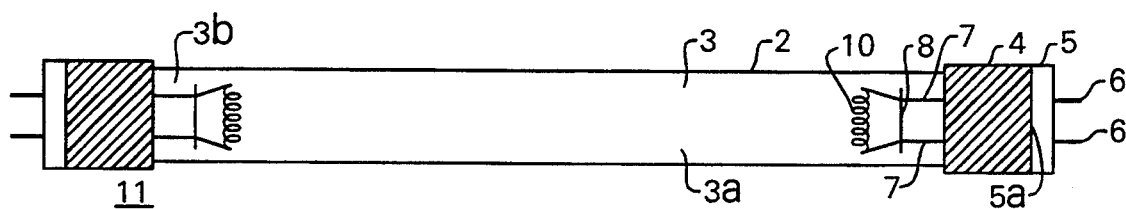
FIG. 1 shows a partly sectional, elevational side view of a tube embodying aspects of the invention.

Referring now to FIG. 1, one embodiment of the present invention is described. A tube 1 is shown having a linear elongated configuration. Tubes incorporating the invention have been made with lengths from 4 inches to 10 feet, and in varied shapes. The tube 1 has at each end a stem 11.

Disposed between the stems 11 is an envelope 2. Envelopes having linear or U shapes are preferred, although bulb-shaped envelopes may be used. The envelope 2 may be made from any of the materials well known to those skilled in the art. However, envelopes of hard glass quartz containing low-pressure rare earth components are especially well-suited to the present invention. These envelopes are especially hard and so well-suited to tubes embodying the invention. Envelopes made from such glass do not soil or degrade ultraviolet energy as rapidly as soft glass materials used in the past.

Figure 1A:
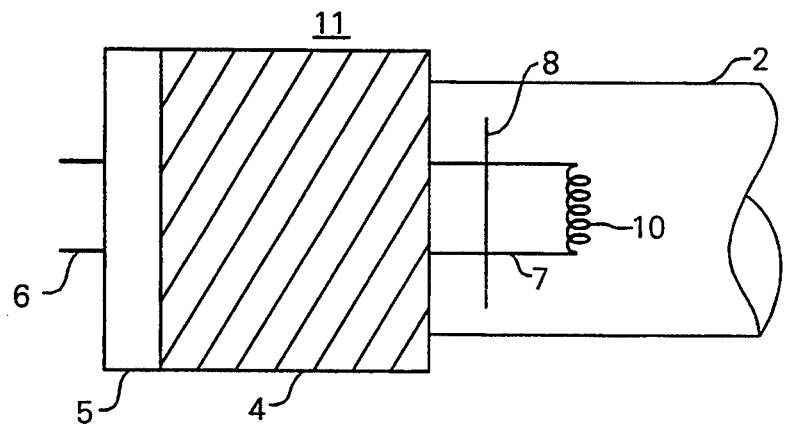
FIG. 1a shows a cutaway partial side view of one end of a tube embodying aspects of the invention.

Referring now to FIG. 1a, there is shown one end of a tube embodying aspects of the invention. The end includes stem 11 and attached section of the envelope 2. The stem 11 includes leads 6, tube base 5, heat sink 4, filament holders 7 and electrode 10.

The leads 6 are electrically connected to respective filament holders 7. The leads 6 provide electrical contacts to the tube.

Typically, the tube base 5 is constructed of an electrical and heat insulator such as ceramic.

The heat sink 4 provides additional cooling to the end of the tube. The heat sink 4 is preferably a good heat conductor such as aluminum. The heat sink 4 surrounds the envelope 2 and is preferably secured to the tube base 5. In the preferred embodiment, the heat sink 4 is crimped to the base 5, although other methods may also be employed. The heat sink 4 provides increased cooling of the envelope at a cooling region 3b as explained below. Also, the heat sink 4 draws heat from the tube base 5, thereby reducing heat reflection from the base 5 into the tube 1 and increasing the durability of the base 5.

The filament holders 7 are made from well known materials. However, according to the invention, the filament holders 7 have extended length, thereby placing the electrode 10 a certain distance from the tube base 5.

The electrode 10 consists preferably of a thin, coiled metal wire filament, such as of tungsten, and is electron emitting when heated. However, anything through which the high frequency voltage will conduct can be used, and in any shape, such as round or hollow. The electrode 10 is preferably situated at the end of the envelope near the stem 11. These electrodes 10 are heated to an electron emitting temperature directly by the discharge current flow therethrough. Materials for and construction of electrodes are well-known in the art.

One additional element is shown—the spacer 8. The spacer 8 and the base 5 define a cooling region 3b inside the envelope. The spacer 8 is generally platelike, with scallops 8b. The spacer 8 helps to establish the convection current, by acting as a physical barrier to moving gas and as a thermal barrier. The spacer 8 in each of the stems 11 at the ends of the tube 1 define a radiation region 3a inside the envelope.

Figure 2:
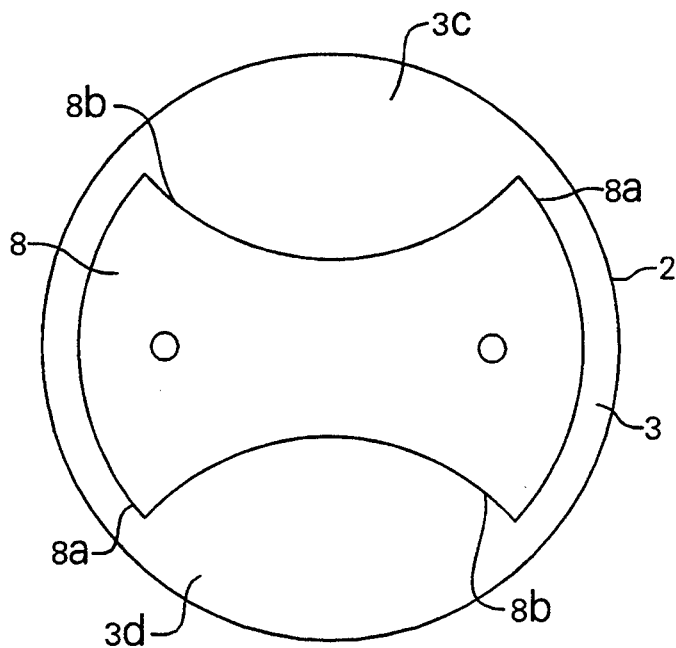
FIG. 2 shows a cross-sectional partial view of a tube embodying the invention.

Referring to FIG. 2, a cross-sectional partial view of a tube embodying the present invention is shown. The spacer 8 is shown surrounded by the envelope 2, but does not contact the envelope 2. The filament holders 7 and attachment wire 12 are not shown in this Figure. The spacer 8 is preferably made from a non-conductive material having high heat and radiation reflecting properties, for example mica. Such materials are well known to those skilled in the art. The spacer 8 has two opposing convex surfaces 8a and two opposing concave surfaces 8b. The inner wall of the envelope 2 and the concave surfaces 8b of the spacer 8 defines flow regions 3c and 3d.

As discussed, a convection current is established inside 3 the tube 1 between the cooling region 3b and the radiation region 3a. It is believed that hot gas enters the cooling region 3b from the radiation region 3a through one flow region (e.g. 3c), and cooled gas exits the cooling region 3b to the radiation region 3a through the other flow region (e.g. 3d). In this way, the convection current created inside the tube 1 may be controlled by the shape of the spacer 8.

Only the heat sink 4 and tube base 5 contact the envelope 2. Preferably, the spacer 8, electrode 10, and filament holders 7 do not contact the envelope 2.

A tube having the cooling region of the invention accomplishes a self-regulating condition and permits the use of an extremely high operating current of approximately 800–1,000 mA. The self-regulating condition is a thermal equilibrium, creating a controlled heat distribution in the tube. This condition consists primarily of a convection current inside the envelope. The convection current is established between the cooling region 3b and the radiation region 3a. One feature of the self-regulation is that the pressure of the convection current is greater than without the self-regulation. As discussed, a normal tube is rated at just 400 mA. Tubes embodying the invention do not suffer from the ultraviolet degradation and shortened life (approximately 1,000 hours) caused by extra high interior and seal temperatures.

In addition to the thermal convection current, it has been observed that mercury in the tube also has a convection current. Heated mercury in the radiation region 3a circulates into the cooling region 3b and cools. When the mercury cools it coagulates and can be observed on the inside of the container 2.

The energy and heat in the radiation region 3a are fairly well distributed. The highest heat is found closest to the electrodes 10, and there is a gradient between the electrodes and the inside edge of the base 5a. Thus the lowest temperature and pressure are found at the inside edge of the base 5a.

In one embodiment of the invention, the tube 1 is linear and elongated and has approximate overall length of 17½ inches. The envelope has outer diameter of approximately ¾ inch. The heat sink 4 is approximately 1¼ inches long. The shield 8 is located ½ inch further into the tube 1 from the inner edge 5a of the heat sink 4. The envelope 2 is ½ inch thick. When employing the invention in such a tube, the tube life has been extended to as many as 10,000 hours, with an average of 7,500 hours. The preferred embodiment has been shown including spacer 8, shield 9, and heat sink 4. However, these elements are cumulative, so that the desired effects may be achieved through employment of any one of these, or similar components.

Figure 3:
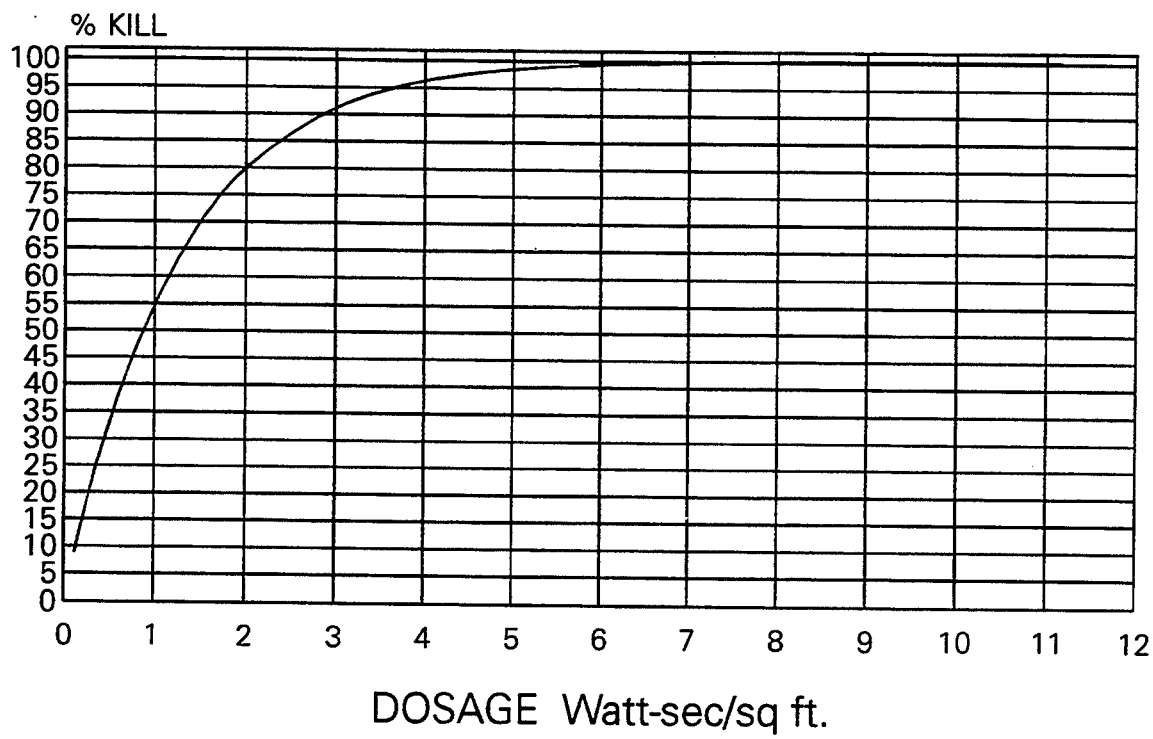
FIG. 3 is a table showing percentage kill of E-Coli bacteria when exposed to ultraviolet light.

As discussed, electric discharge devices have been used to sterilize air. FIG. 3 is a chart showing the effectiveness of 254.7 nm ultraviolet radiation to kill *E-Coli* bacteria. As can be seen, for dosages of 3 W-s/sq. ft. and greater, over 90% of the bacteria are killed. The tube of the invention is particularly well-suited to such applications.

In an air conditioning system embodying one aspect of the invention, it has been found that skin-effect cooling does not drop ultraviolet output. It has been found that when 400 feet per second of air is blown over sterilizers embodying aspects of the invention, and the air is above 54° F., ultraviolet output will increase as much as 10%–40%. Such high efficiency output leads to more effective sterilization.

Figure 4:
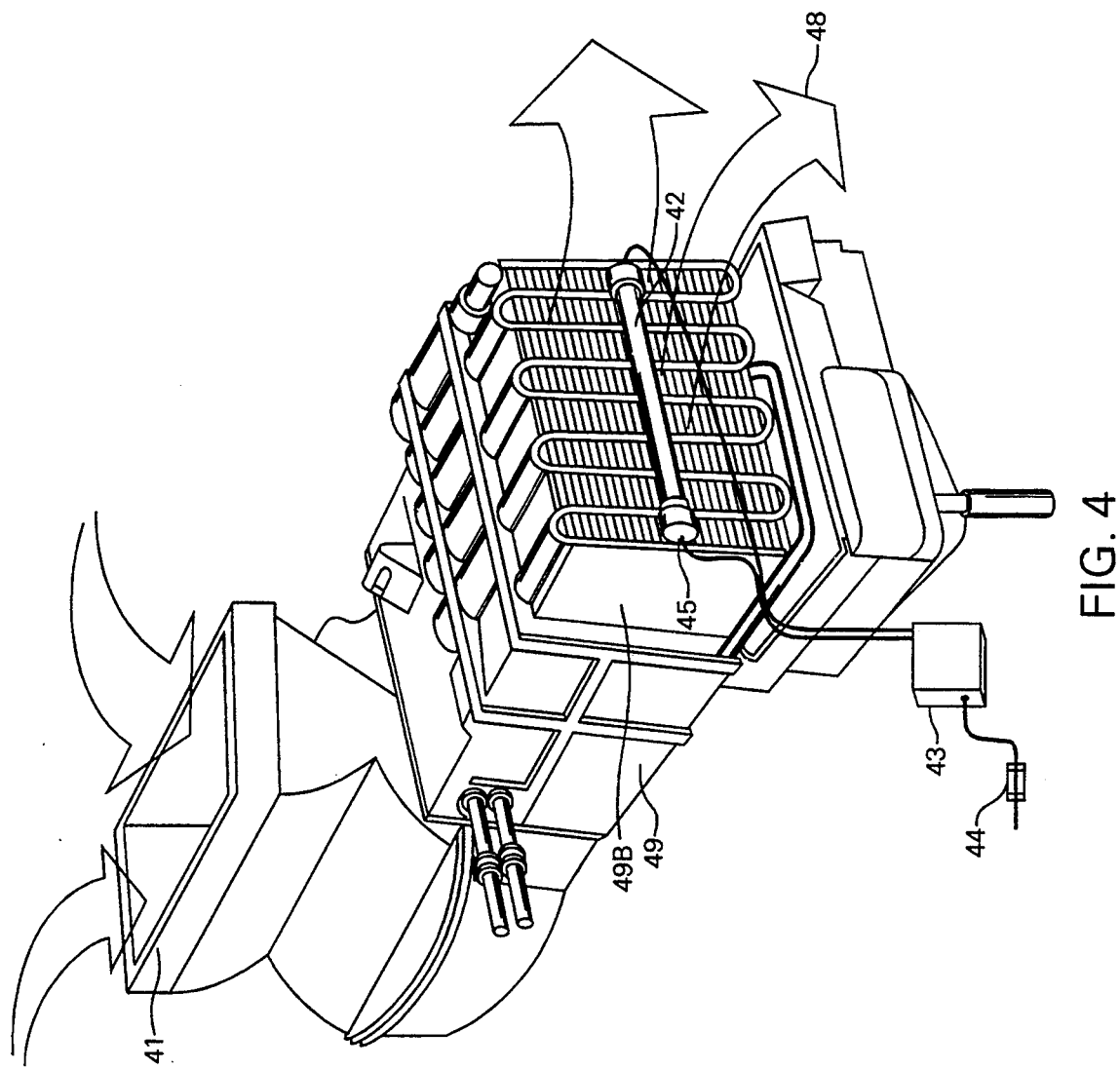
FIGS. 4 and 5 show a partial elevational view of an automobile air conditioning system employing embodiments of the invention.

Referring now to FIG. 4, an embodiment of another aspect of the invention is shown as installed in a vehicle's air conditioning system. As shown by the arrows, air is drawn into the intake 41 of the air conditioner and drawn into the evaporator housing 49, passing through the evaporator coil 49b to pass out of the air conditioning unit as sterilized air 48. The sterilizer itself comprises a compact electric discharge device that may easily be installed in a vehicles's air conditioning unit. The sterilizer includes an ultraviolet tube 42, wire harness and lamp plugs 45, a power supply 43 and a fuse 44. The fuse 44 is connected to a lead which is connected to the vehicle's electrical system as is known in the art. The power supply 43 is matched to the vehicle's electrical system.

Figure 5:
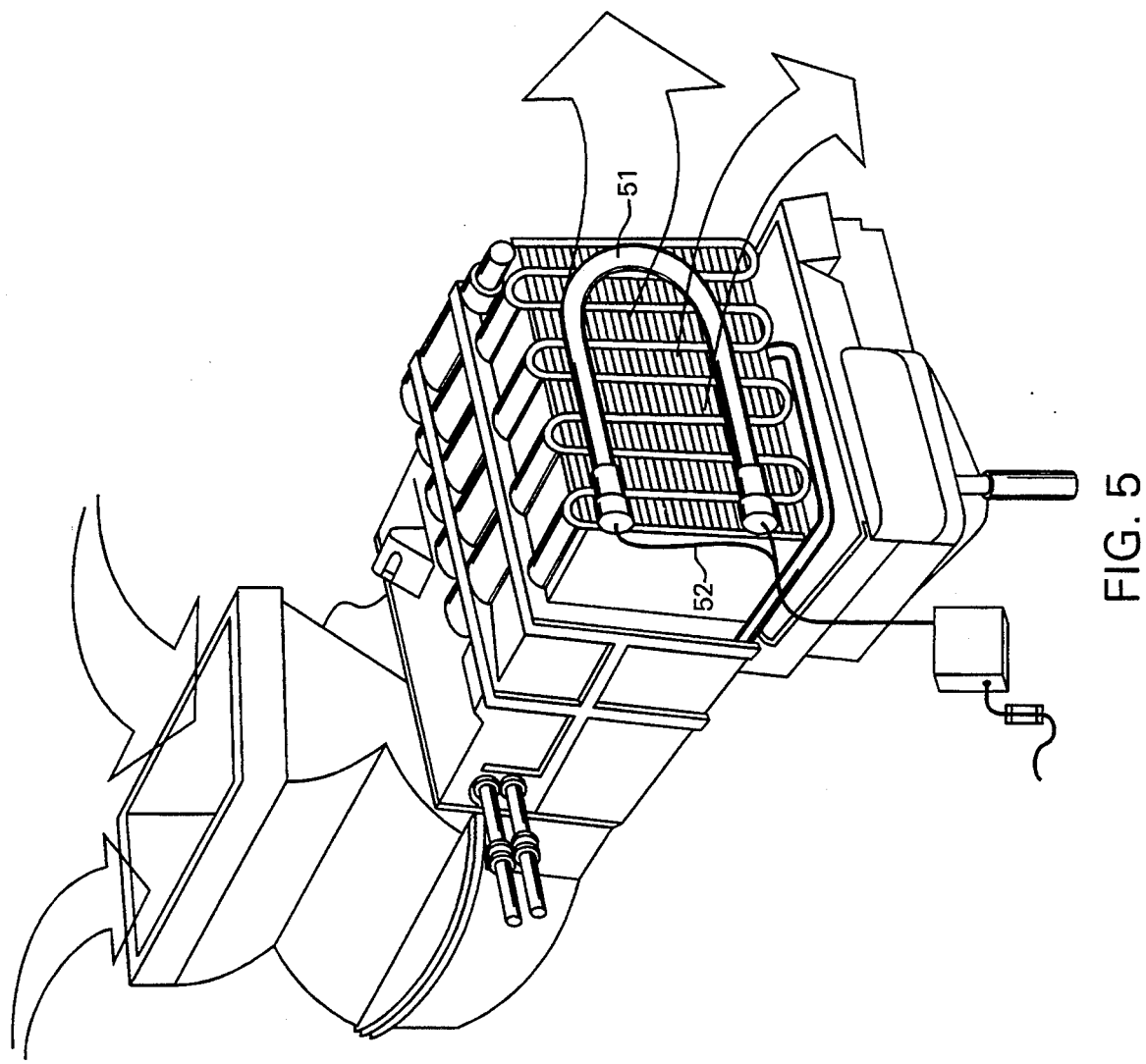

In FIG. 5 there is shown an alternative embodiment of the air sterilizer as shown in FIG. 4 utilizing a U-shaped sterilizer tube 51 with a special wire harness and mount 52. The shape of the sterilizer tube and the type of mount may be selected to most advantageously adapt to the vehicle's existing air conditioning system.

Figure 6:
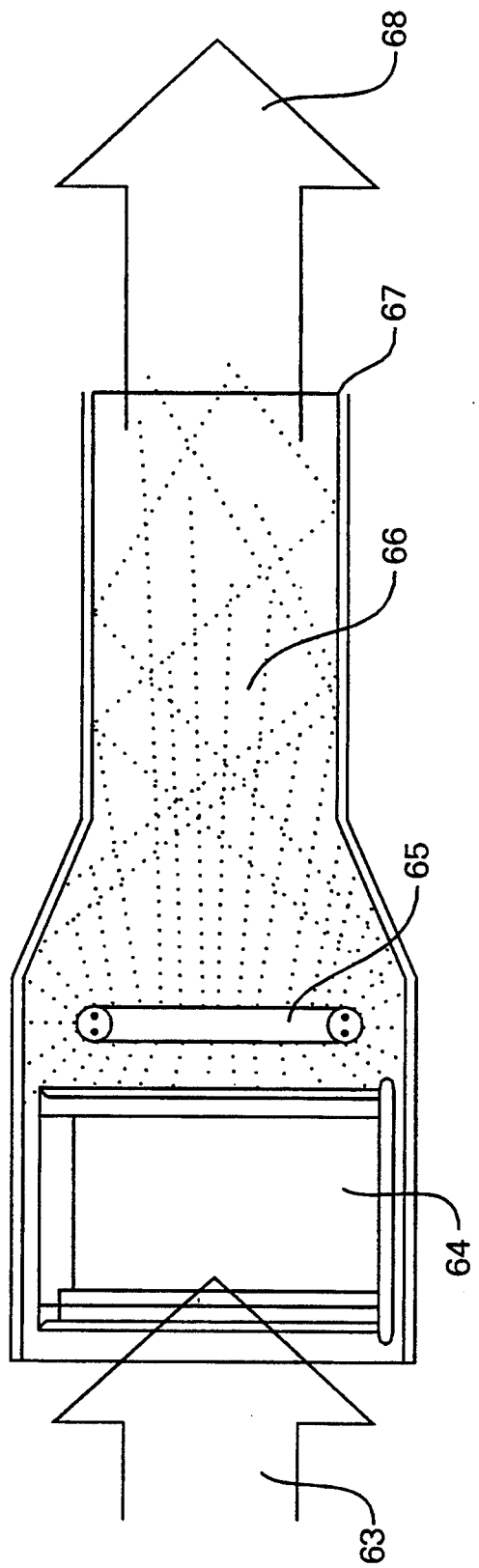
FIG. 6 shows a cutaway side view of one embodiment of the invention showing reflected ultraviolet light.

As shown in FIG. 6, contaminated air 63 entering the sterilizing chamber 66 of the air conditioning system emerges after sterilization as sterilized air 68 having 40-99.9% of the airborne contaminants made harmless. The contaminated air 63 on its way through the air conditioning system passes through the evaporator coil 64 and moves past the sterilizer tube 65. Preferably, the air conditioning duct is reflective of the ultraviolet energy (254 nm). The reflected material directs the ultra violet back toward the evaporator coil and into the drip pan—primary sites for growth of molds and fungi—to intensify the sterilization effects. This reflective material 67 may be paint or foil or other materials as are known in the art. Although FIGS. 4-6 show the sterilizer unit downstream from the evaporator coil, the sterilizer may also be situated upstream from the evaporator coil. However, an upstream unit will not provide the same level of sterilization of the evaporator coils as a downstream unit.

Vehicle air conditioning systems have been found to be especially well-suited to electric discharge devices embodying the invention. The solid state design of the ballast is designed to work with a vehicle's 12 v DC electrical system. The solid state electronics are rugged, and through careful selection, can withstand the temperature extremes on the order of 0°-140° F. Since the tube is thermally self-regulating, it too withstands the broad temperature range, while continuing to emit ultraviolet radiation. Even though ultraviolet radiation output will drop due to skin-effect cooling, as low as 45%, the high output of the tube results in a practical amount of ultraviolet radiation emitted. Furthermore, because the state of the tube changes (temperature, ultraviolet output), the ballast is uniquely adapted to supply the proper electricity to the tube.

Figure 7:
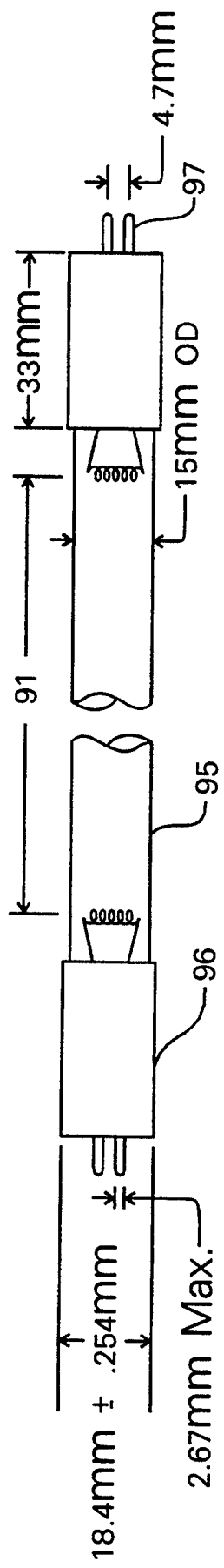
FIG. 7 shows a partial view of an embodiment of the invention.

In FIG. 7 there is shown an embodiment of the invention demonstrating the range of preferable dimensions. These include arc length 91 from 45 mm to 12 feet in any shape; and a base face to base face length of 125 mm to 13 feet. The bases 5, constructed of metal and ceramic for longer life, have a preferable outer diameter of 18.4 mm±0.254 mm. The leads 6 extending from the base 5 have width of 2.67 mm max and are spaced 4.7 mm apart. These leads 6 extend preferably 7.24 mm from the base. The envelope 2 preferably has an outer diameter of 15 mm. The base 5 preferably has overall length of 33 mm.

It will thus be seen that the objects set forth above, and those made apparent from the preceding description, are efficiently attained. Since certain changes may be made without departing from the scope of the invention, it is intended that all matter contained in the above description shall be interpreted as illustrative and not in a limiting sense.

I claim:

1. An electric discharge device comprising a ballast and a sealed tube containing a vaporizable material, the tube comprising a tube base, an elongate hollow envelope having two ends, electrodes partially disposed within the envelope at each end and electrically coupled to the ballast, and means for establishing at least two regions within the envelope when the electrodes are energized, one region being cooler than the other region, wherein when the electrodes are energized, the tube emits radiation omnidirectionally.

2. The device of claim 1 wherein the envelope is cross-sectionally round and has at least one end, the establishing means comprises a heat sink which defines a cross-sectionally round aperture which surrounds a part of the envelope at the end.

3. The device of claim 2 wherein the heat sink aperture contacts the envelope so that the heat sink is thermally coupled directly to the envelope.

4. The device of claim 3 wherein the heat sink aperture contacts the tube base.

5. An electric discharge device comprising a tube comprising an elongate envelope having two ends and containing a free-flowing material, an electrode disposed at each end, and a ballast electrically coupled to the electrodes for energizing the electrodes, the envelope defining a cooling region and a radiation region, wherein when the electrodes are energized, the free flowing material circulates into the cooling region and cools and is heated in the radiation region, and the tube emits radiation omnidirectionally.

6. An electric discharge device as set forth in claim 5, further comprising means for cooling the material when the electrode is energized.

7. The electric discharge device of claim 9 wherein the cooling means comprises a heat sink.

8. The electric discharge device of claim 7 wherein the envelope comprises at least one end, wherein the heat sink surrounds and contacts at least part of the envelope at the end.

9. An electric discharge device comprising:
a sealed tube comprising an elongate envelope having two ends and defining an inside region, and an electrode at least partially disposed in the inside region at each end;
a ballast electrically coupled to the electrodes for energizing the electrodes; and
means for effecting a convection current in the inside region following energization of the electrodes sufficient to provide a thermal equilibrium for the tube,
wherein when the electrodes are energized, the tube emits radiation omnidirectionally.

10. A method for sterilizing air comprising:

(a) providing an electric discharge device, the device comprising an envelope containing an electrode and a vaporizable material, wherein the device, when energized, emits radiation on the order of magnitude of 254 nm;
(b) energizing the electrode using electricity of 50-300 KHz to produce a power density of at least 11 $\mu W/cm^2$.
(c) passing the air into the emitted radiation.

11. A method for sterilizing air comprising:
(a) providing an electric discharge device comprising a tube comprising a hollow envelope and an electrode disposed at least partially within the envelope and a vaporizable material disposed within the tube;
(b) energizing the electrode whereby the tube emits radiation;
(c) establishing within the tube a convection current having a pressure sufficient to maintain a thermal equilibrium in the tube;
(d) passing the air into the emitted radiation.

12. A sterilizing unit for use in a vehicle's air conditioner and electrical system comprising: a sterilizing chamber; a tube in the chamber comprising an envelope, an electrode and a vaporizable material; at least one lamp plug attached to the tube; a ballast operable with the vehicle's electrical system; means for establishing at least two regions within the envelope when the electrode is energized, one region being cooler than the other region; and a wire harness comprising a plurality of electrical wires connecting the power supply to the plugs.

13. The sterilizing unit of claim 12, wherein at least part of the sterilizing chamber is reflective of ultraviolet light.

14. The sterilizing unit of claim 12 wherein the tube, when energized, emits radiation on the order of magnitude of 254 nm.

15. The sterilizing unit of claim 12, the air conditioner including an evaporator coil, wherein the sterilizing unit is mounted upstream from the evaporator coil.

16. The sterilizing unit of claim 12, the air conditioner including an evaporator coil, wherein the sterilizing unit is mounted downstream from the evaporator coil.

17. A method for sterilization in a vehicle comprising:
(d) providing an electric discharge device in a sterilizing chamber; a tube in the chamber comprising an envelope, an electrode and a vaporizable material; at least one lamp plug attached to the tube; a ballast operable with the vehicle's electrical system; a wire harness comprising a plurality of electrical wires connecting the power supply to the plugs;
(e) energizing the electrode using electricity of 50-300 KHz so that the tube emits at least 11 $\mu W/cm^2$ of ultraviolet light.
(f) moving air through the sterilizing chamber.

18. The method of claim 17 wherein the sterilizing chamber is coated with an ultraviolet light reflective material.

19. A sterilizing unit for use in an air conditioner comprising: a sterilizing chamber; a tube in the chamber comprising an envelope and an electrode; a vaporizable material sealed within the tube; a ballast electrically coupled to the electrode for energizing the electrode; and means for effecting a convection current within the tube; wherein when the electrode is energized, the tube emits radiation including heat radiation, and the effecting means effects a convection current which provides a thermal equilibrium for the tube.

20. A device for eliminating odor in an air conditioning system, the air conditioning system including an evaporator coil, the device comprising: a tube comprising an envelope and an electrode at least partially disposed within the envelope, a ballast electrically coupled to the electrode for energizing the electrode, and a vaporizable material sealed within the tube; wherein when the electrode is energized, the tube emits radiation directed at the evaporator coil and a convection current is established within the tube having a pressure sufficient to maintain a thermal equilibrium in the tube.

21. The device as set forth in claim 20 further comprising means for establishing a thermal equilibrium in the tube.

22. The device as set forth in claim 20 wherein the tube further comprises means for establishing two regions within the envelope when the electrode is energized, one region being cooler than the other.

23. The device as set forth in claim 20 wherein the electrode is energized using electricity of 50-300 KHz.

24. A method for eliminating odors in an air conditioner comprising providing an air conditioner comprising an evaporator coil, energizing a tube that produces radiation and establishing within the tube a convection current having a pressure sufficient to maintain a thermal equilibrium in the tube, and directing the radiation at the evaporator coil of the air conditioner to at least partially sterilize the coil.

25. An electric discharge device comprising an elongate envelope having two ends, the envelope containing at least one electrode at each end and a vaporizable material, a heat sink surrounding and contacting at least part of the envelope at the end, and a ballast electrically coupled to the electrodes for energizing the electrodes, wherein when the electrode is energized, the tube emits radiation omnidirectionally and a convection current is established within the tube having a pressure sufficient to maintain a thermal equilibrium in the tube.

26. An electric discharge device comprising a ballast and a sealed tube containing a vaporizable material, the tube comprising a tube base, a hollow envelope having at least one end, an electrode partially disposed within the envelope and electrically coupled to the ballast, a spacer disposed within the envelope, the spacer spaced between the electrode and the end, and means for establishing two regions within the envelope when the electrode is energized, one region being cooler than the other region.

27. The electric discharge device of claim 26 wherein the envelope has a central longitudinally extending axis, and the spacer is thin and flat and extends perpendicular to the axis.

28. The electric discharge device of claim 25 wherein the spacer separates the cooler region from the other region.

29. An electric discharge device comprising a tube and a ballast, the tube comprising an envelope containing at least one electrode and a vaporizable material and having at least one end, and means for cooling the vaporizable material when the electrode is energized comprising a heat sink surrounding and contacting at least part of the envelope at the end and a spacer disposed between the electrode and the end.

* * * * *